(12) United States Patent
Tjota

(10) Patent No.: US 6,653,085 B1
(45) Date of Patent: Nov. 25, 2003

(54) CELIAC ANTIGEN

(75) Inventor: Amin Tjota, Williamsville, NY (US)

(73) Assignee: Xybernaut Corporation, Fairfax, VA (US)

( * ) Notice: Subject to any disclaimer, the term of this patent is extended or adjusted under 35 U.S.C. 154(b) by 760 days.

(21) Appl. No.: 09/263,331

(22) Filed: Mar. 5, 1999

Related U.S. Application Data

(60) Continuation-in-part of application No. 09/018,419, filed on Feb. 4, 1998, now abandoned, which is a division of application No. 08/626,243, filed on Mar. 29, 1996, now Pat. No. 5,716,794.

(51) Int. Cl.[7] .................. G01N 33/53; C07K 17/00; C07K 16/00
(52) U.S. Cl. .................. 435/7.1; 435/7.92; 530/350; 530/387.1
(58) Field of Search ................ 435/7.92, 7.1; 424/184.1, 193.1, 130.1, 142.1; 530/350, 387.1

(56) References Cited

U.S. PATENT DOCUMENTS 4,302,385 A * 11/1981 Bohn et al. .................. 260/112

* cited by examiner

*Primary Examiner*—James Housel
(74) *Attorney, Agent, or Firm*—Arthur S. Cookfair, Pat. Agent; James J. Ralabate, Esq.

(57) ABSTRACT

In this invention a novel antigen and a novel antibody-antigen complex are provided for screening patients suspected of having celiac disease. The antigen is prepared by starting with human placenta tissue which is perfused with a hepes and collagenase buffer to obtain a single cell suspension. This suspension is enriched to obtain an enriched protein portion and then separated out to obtain an embryonic celiac antigen (ECA). This ECA is used with serum from patients to effect binding of ECA with IgA in the serum while applying a human IgA antibody to the serum. The results are then read on a spectrophotometer to confirm or negate the presence of celiac disease.

2 Claims, No Drawings

CELIAC ANTIGEN

This invention relates to a novel antigen and, more specifically, to a novel antigen useful as a screening assay for celiac patients. This application is a continuation-in-part of application Ser. No. 09/018,419, filed Feb. 4, 1998 for Novel Celiac Antigen, now abandoned, which in turn is a divisional application of application Ser. No. 08/626,243, filed Mar. 29, 1996 for Celiac Antigen, now U.S. Pat. No. 5,716,794.

BACKGROUND OF THE INVENTION

Several known antigens are known and are presently being used for identifying celiac disease in both adults and children. Some of these antigens and the screening procedures are outlined in the articles "Precipitins to antigens of wheat and cow's milk in celiac disease" by Heiner D C, Lahey M E, Wilson J F, et al., published in 1962 in *J. Pediatr.* 61,814; "A reliable screening test for childhood celiac disease: fluorescent immunosorbent test for gliadin antibodies. A prospective multicenter study," published in 1983 in *J. Pediatr.* 102:655–60; "Gliadin antibodies in celiac disease" published in 1983 in *J. Pediatr.* 102:711–2. There are also several other papers and publications concerned primarily with tests for detecting celiac disease. While some tests have been found to be somewhat effective and at least sometimes accurate, there is a need for a more reliable antigen and uniform interpretation of screening assays for celiac patients.

Childhood Celiac Disease (CD) is a condition characterized by malabsorption and growth disturbances in association with a specific histological lesion of the small intestine. Patients with malabsorptive symptoms have been found to date to the second century AD. In 1950's Dicke, a pediatrician found the relationship between grain consumption and severe malabsorption condition. He noticed that during WWII children in Holland with malabsorptive symptoms improved when wheat and rye flour were unobtainable and that the condition reappeared after wheat flour was again made available. He and his associates were also credited with identifying gluten, the water-insoluble protein fraction in wheat, as the toxic dietary substance responsible for the syndrome, noting that symptoms subside in response to gluten elimination.

Recently, the European Society for Pediatric Gastroenterology and Nutrition (ESPGAN) revised the criteria for the diagnosis of gluten sensitive enteropathy (GSE), celiac disease. The previous criteria set forth in 1969 required at least three small intestinal biopsies. The salient histological features of CD were required at the initial suspicion of the enteropathy. The histological findings were expected to resolve following a period of gluten elimination and be reinduced during a gluten challenge phase of establishing the diagnosis. Since then, the success of newer diagnostic markers—antigliadin, antireticulin and antiendomysial antibodies—in serving as indicators of active disease has prompted a revision of the criteria. Current requirements include a characteristic histologic appearance of the mucosa at the time of presentation with resolution of symptoms following gluten elimination. The presence of the previously mentioned circulating antibodies at time of diagnosis and disappearance following gluten withdrawal adds weight to the diagnosis especially in those who are asymptomatic.

Few controversies in the discipline of Pediatric Gastroenterology are viewed with less emotion that the selection of the best serologic screening test for celiac disease. The discovery of circulating antibodies to gliadin (AGA), reticulin (ARA) and the endomysium (EMA) have brought us closer to the discovery of a simple non-invasive screening test for establishing the diagnosis; but none are universally accepted as being pathognomonic indicators of the condition. Although none can be considered, as yet, pathognomonic, the serologic antibodies can still be used for screening and aid in diagnosis if one realizes their limitations and interprets their presence or absence in light of the clinical situation faced. We are approaching a better understanding of their roles and interrelationships.

The above mentioned present day serological markers are circulating antibodies which serve as one piece of evidence for the immunological nature of the disease. Circulating antigliadin antibodies (AGA) represent antibodies to the cereal protein, which presumably is absorbed intact across the intestinal mucosa. AGA have been extensively investigated since initial descriptions appeared in the late 1950's and early 1960's. Techniques for detection have evolved over the years varying from precipitating antibodies to cereal proteins, microimmunodiffusion, radioimmunoassay, binding serum antibodies to wheat grains and detection by fluorescent horse antihuman IgG. The first ELISA method appeared in 1977 and is defined and described in detail in Hekkens W T, Van Twist M: Physiological role of antigliadin antibodies and their appearance in celiac disease; Chorzelski T P Beutner E H, Kuman V, Zalewski T K, eds. Serologic Diagnosis of Celiac Disease. Cleveland:CRC Press, 1990: 2A: 21058 and Hekkens W T, VanLems-Kan P H, Rosekrans PCM: Bepaling van gliadin antistoffen met de ELISA-Techniek. Ned Tijdschr Geneesk 121, 1908, 1977. The differences in techniques for detection led to problems with standardization and therefore reproducibility between studies. Several authors have attempted to improve the sensitivity of the method of detection by using a diffusion to gel ELISA as described in Lindberg T, Nilsson L. Borulf S, et al.: Serum IgA and IgG gliadin antibodies and small intestinal mucosal damage in children. J. Pediatr Gastroenterol Nut 4, 917, 1985. It is understandable that even similar techniques such as ELISA may yield difference results because gliadins are a complex mixture of proteins that contain at least 40 different components for a single variety of wheat. Several authors have attempted to improve the sensitivity of detection method by using gliadin fractions or peptides as antigens. In one study, different gliadin peptides were found to have differing reactivity to serum antibodies of untreated celiac patients. However, other authors report that there are no demonstrable differences in ELISA values using different gliadin fractions as antigens. Discordant results, therefore, have been reported despite the use of similar methodologies such as ELISA.

Further controversy exists regarding the value of the specific class of AGA antibodies in the diagnosis of celiac disease. Some investigators advocate IgG class AGA whereas the IGA-AGA are favored by others. In studies using purified gliadin peptides as antigens in RIA or ELISA, IGA antibodies seem to have greater specificity to celiac disease and IgG antibodies seem to be more sensitive. The usefulness of gliadin antibodies for diagnosis, however, is open for criticism because their sensitivity and specificity varies so much from study to study. Figures for specificity range between 65–100% for IgA antibodies and 50–100% for IgG antibodies. Sensitivity reports for IGA antibodies range between 52–99.9% and for IgG between 82–100%. Unfortunately, IgG antibodies can be found in normal controls as well as other disease controls such as Chrohn's disease, liver disease and other G.I. disorders. IgA antibodies, on the other hand, although being specific for celiac disease, are not found in all celiacs. Additionally, IgG are found to increase with age in normal controls making them unsuitable for diagnosis in older age groups. The combined use of the two classes of antibodies, therefore, has been proposed by some authors as improving the sensitivity and specificity of the AGA for diagnosis. At least one recent report did not find advantage in combining each. The merit of using the IgG AGA seems to be in its ability to discriminate those 3% of celiac patients who are also IgA deficient and therefore would not be identified by screening for IgA AGA.

Gluten challenge is followed by an increase in titres of both IgA and IgG-class antibodies and titres fall with gluten exclusion. IgG antibodies take longer to decline than IgA antibodies. They may take more than six months to decline whereas IgA antibodies decline by 2–6 months. Their appearance is stated to occur before symptoms become overt. IgA AGA antibodies are therefore suitable to monitor dietary compliance and also response to gluten provocation.

Antireticulin antibodies (ARA), on the other hand, have been investigated since initial reports in the 1970s. The ARA were first described as antibodies reacting with connective tissue fibers around hepatic sinusoids, and blood vessels as well as perilobular, periglomerular and occasional glomerular staining of the kidney and also for fine staining of the stroma between gastric glands. ARA reacted with connective tissue of both rat and human organs and appeared to be directed against reticulin fibers in these tissues. The antibody was best detected by indirect immunofluorescence using rat liver and kidney as the substrate. The ARA do not react with type III colagen, noncallagenous reticulin components or fibronectin and they seem to be specific for other unidentified connective tissue components. Several staining patterns by indirect immunofluorescence were found to occur. An R 1 pattern was exhibited by celiac and dermatitis herpetiformis patients. This pattern was characterized by staining of peritubular and periglomerular fibers in the kidney and fluorescence in portal tracts of rat liver. In contrast to other ARA subtypes, it also reacted with human tissues, although some authors disagree to the human expression. They insist that the reticulin antigen are specifically expressed in rodent but not in primate tissues. ARA can be of the IgG or IgA class but IgM antibodies do not occur. IgG antibodies usually occur in conjunction with IgA ARA. The specificity of IgG-ARA for GSE is controversial. The IGA-class ARA seem to be disease specific and sensitive indicators of gluten-sensitive enteropathy. The range of specificity reportedly lies between 59–100% and sensitivity between 30–95% indicating somewhat similar sensitivity and specificity as the IgA-AGA, however, some authors may argue that the R-1 ARA are probably more specific for celiac disease than the gliadin antibodies. However, the R-1 ARA also have been reported in patients with Crohn's disease and occasionally with other conditions. The significance of the R-1 ARA is uncertain, however, the association between it and untreated celiac disease is well established and it will disappear from the circulation following the start of a strict gluten-free diet. Sensitivity and specificity reports are subject to differences in populations studied. For example, some exclusively looked at specific populations such as India, where one does not expect to find patients with inflammatory bowel disease, the authors found that R-1 ARA were 100% specificity with 85% sensitivity.

A third group of circulating tissue antibodies, the endomysial antibodies (EMA), are gradually gaining acceptance as sensitive and specific markers of celiac disease. These are primarily IgA antibodies directed against the intermyofibril substance of the smooth muscle which may correspond either to a reticulin-like structure or a surface component of smooth muscle fibrils. This antigen may also be expressed around lamina propria structures around intestinal crypts, muscularis mucosa and smooth muscle fibers to which "human jejunal antibodies" are directed. Unlike R-1 ARA which is reported to react with human and various rodent tissues, EMA has been demonstrated to be species-specific, reacting only with the endomysium in the gastrointestinal tract of primates. They are detected by indirect immunofluorescence using monkey esophagus tissue sections. The sensitivity and specificity of the EMA approaches but is not 100%. Some false positive cases have been reported. A case of cows' milk protein allergy and one with Giardia lamblia have been reported. In addition, one celiac patient was discovered who was IgA and IgG EMA negative on presentation and during gluten challenge. Therefore, we believe that false negative cases are less common that false positive cases but that they do exist and will continue to be reported. Absence of EMA may be more frequent in celiac patients younger than two years than in older individuals. In a recent report, three children with positive and four with weak positive results did not have celiac disease. Sensitivity was found to be 100% with specificity at 97%. In another study which compared EMA, AGA and ARA in an Israeli group of celiac patients, specificity was 98% and sensitivity was 97%. In this study, the EMA appeared to be the most reliable serologic marker for the diagnosis of celiac disease. The positive predictive value of the EMA and ARA were comparable (97% and 100%, respectively), however, the EMA had the highest negative predictive value (98%). Additionally, EMA were found to be more diet sensitive. By three months of gluten withdrawal more children were negative for EMA than AGA or ARA. High EMA titres appear quicker in response to gluten challenge. No serologic test at present therefore enjoys a 100% sensitivity and specificity. However, of all the markers, we believe the EMA is presently the best serologic test based on our interpretation (bias, if you will) of currently available data.

The occurrence of false positive and false negative results with the above markers requires some comment. Deficiencies exist with the uniformity of interpretation of the methodologies of detection of the above antibodies using indirect immunofluorescence. When one encounters reports of false negative cases in using indirect immunofluorescence, one is tempted to question the technique and interpretation of the test systems. Also, what titre should be considered positive? Should weakly stained sections at low serum dilution be considered positive? One also needs to consider whether the patient is IgA deficient when IgA, AGA, ARA or EMA are being used. Indeed, some investigators advocate that IgA AGA do not offer advantage over IgG AGA and that subjects with isolated selective IgA deficiency and celiac disease would be better picked up by screening for both IgG-AGA and IgG-ARA since IgG-AGA is less specific and are commonly found in non-celiac subjects with selective IgA deficiency.

When one discovers false positive cases for EMA or either AGA or ARA, one wonders whether these may be latent celiacs. Truly, the antibodies are demonstrated in these cases but why they are present remains an enigma. Maybe one should not consider this as "false" positive. Only follow-up studies will determine whether these individuals develop celiac disease. Indeed, this type of situation has been recently addressed. Seven of 25 patients exhibiting ARA or AGA and having normal small-bowel mucosal villous architecture at presentation were found to subsequently develop villus atrophy after a follow-up period of 1–7 years. Patients who are "false" positive for EMA may also prove to develop the histopathologic features of celiac disease in the future. Future studies will elucidate this issue. With regard to false negative cases, however, there seems to be very few published cases of celiacs who do not possess the EMA.

Since it is becoming generally accepted that subclinical celiac disease is common in the general population, the use of screening tests in clinical studies is become increasingly important. Many patients who are free of major symptoms are being identified to possess the typical histological features of Celiac Disease. They are discovered during studies addressing the incidence of celiac disease using serologic markers as screening tests in high risk populations such as family members, patients with diabetes, short stature or in the general population. When one considers the silent celiacs, the true incidence of the disease in the USA and Europe may be higher than reported. It was found using EMA that the rate in family members was 8% and those with diabetes was 4% and short stature 1.7%. These are similar figures to those reported in European studies. However, the incidence in patients with major symptoms was only 1.29 per 10,000 live births which is much lower than the mode of 1:1,000 reported in European centers. Studies are being awaited with great interest that address the incidence of silent celiacs in both populations. Certainly, the incidence of those with major symptoms is much less than Europe.

The efforts to discover the best screening test for celiac disease and efforts to diagnose every last celiac have vastly overshadowed and outnumbered studies of the pathophysiology of the disease. While gliadin antibodies were report some 30 years ago, work on characterizing the toxic component(s), both in vivo and in vitro, has not been completed. The molecular mechanism behind the pathogenesis of CD is still unsettled but the immunological aspects of the disease have attracted great attention both in the proposal of pathogenetic mechanism and in the efforts to establish a serodiagnostic test for CD.

The different gliadin polypeptides can be separated into four groups, the alpha, beta, gamma and delta fractions by electrophoresis at acidic pH. The molecular weight of a toxic gliadin in the gamma fraction has been recently reported to lie between 35–45 kd. Many hypothesis have been proposed to explain the pathomechanism of the observed gliadin induced enteropathy. Studies have been limited to investigations of lymphoctye populations and cytokine production or toxic peptides acting as lectins which induce cell death. These seem promising, serve to direct future studies at immunologic reactions associated with tissue injury but definitive statements regarding pathophysiology cannot yet be made. Furthermore, the mechanism of generation of the antigliadin is uncertain. There are even less reports which address the reticulin and endomysial antibodies. One expects that the identification and characterization of the antigens to which these antibodies are directed will help in understanding the pathomechanism of the gluten induced enteropathy. It is hoped that future work will be directed at pathophysiology; not only identification and diagnosis. It is expected that characterization of the above antigens will aid in understanding the pathophysiology of the disorder and may even lead to a better understanding of the above diagnostic tests.

SUMMARY OF THE INVENTION

It is therefore an object of this invention to provide a novel antigen useful in screening tests for Celiac Disease devoid of the above noted disadvantages.

A further object of this invention is to provide a novel antigen prepared from human placenta for use in a method to identify Celiac Disease.

Another object of this invention is to provide a substantially reliable antigen having protein molecules of specifically defined molecular weights which when isolated are useful in a screening process for detecting Celiac Disease.

Still a further object of this invention is to provide a novel and substantially more accurate antigen than those previously used in screening patients suspected of having Celiac Disease.

These and other objects of this invention are accomplished, generally speaking, by a novel antigen which in one preferred embodiment is isolated by a method including the identification, isolation and production of an antigen starting with a portion of human placenta. This placenta is perfused using a hepes and collagenase buffer, enriching the resulting composition by condensing it and extracting protein therefrom. The protein is then isolated and prepared for use as an antigen to identify Celiac Disease. This antigen will bind to the IgA/IgG contained in the sera of patients with Celiac Disease. This novel antigen is designated as Embryonic Celiac Antigen (ECA).

Solid phase immunoassay techniques are commonly used to detect the presence of antibodies that react with specific antigens to form an antibody-antigen complex. In such complexes, the binding between the antibody and antigen typically involves one or more of various weak forces, such as, hydrogen bonds, van der Waals forces, electrostatic interactions, and hydrophobic interactions. The formation of an antibody-antigen complex may be demonstrated by further reaction of the complex with a labeled anti-immunoglobulin antibody. In the commonly used enzyme-linked immunosorbent assay (ELISA), the detection involves a color change resulting from the further addition of a secondary antibody labeled with a suitable enzyme, such as, horseradish peroxidase or an alkaline phosphatase. The color change is conveniently detectable by spectrophotometric techniques. It has been found that when an antigen of the present invention (ECA) is reacted with the sera of a celiac disease patient, a novel antibody-antigen complex is formed that serves as an indicator of the presence of that disease. Thus, the complex as well as the method of formation provide method of screening for celiac disease.

The ELISA technique is well known and is described in detail in the following publications: Hekkens, W T, Van Twist, M: Physiological role of antigliadin antibodies and their appearance in Celiac Disease. In Chorzelski T P, Beutner E H, Kumar V, Zalewski T K, eds. Serologic Diagnosis of Celiac Disease. Cleveland: CRC Press, 1990: 2A: 21–58; and Hekkens W T, VanLems-Kan P H, Rosenkrans PCM: Bepaling van gliadin antistoffen met de ELISA-techniek. Ned Tijdschr Geneesk 121, 1908, 1977. This ELISA technique will be used as the methodology for utilizing ECA antigen and a novel antibody-antigen complex formed therefrom, as a screening test for Celiac Disease.

SUMMARY OF THE INVENTION

Thus, this invention provides:
(1) a novel antigen (ECA) to be used in screening for Celiac Disease; and
(2) including a novel method for preparing the novel ECA. Disclosed also herein is a novel antibody-antigen complex and a novel screening process using ECA as the novel antigen.

The antibody-antigen complex of this invention is prepared by a process comprising contacting (1) an embryonic celiac antigen isolated by extraction from a cultured human placenta cell, comprising protein molecules with an isoelectric point (pI) range of from 5.1–5.8 and an apparent molecular weight selected from the group consisting of 55 Kd, 65 Kd, and 110 Kd, with (2) sera from a celiac disease patient. The preferred antigen comprises protein molecules with an apparent molecular weight of 65 Kd.

This novel ECA when used in a screening process will replace the EMA and ARA (indirect Immunofluorescence) procedures above discussed. The accuracy of detecting Celiac Disease using ECA alone or with other procedures is increased about 15% to 20% over prior celiac detecting procedures which is considered very substantial. The placenta that is used is any available human placenta, but the embryonic fetal portion of the placenta is used as the starting material. It is critical to this invention that the eventual protein that is isolated and prepared for use as the antigen has an isoelectric range, i.e., A pI of 5.1–5.8 and a molecular weight of 55 Kd, 65 Kd and 110 Kd or mixtures of these three molecular weights. Those proteins having a different molecular weight did not function as a reliable antigen for Celiac Disease. Competition binding assay was used to identify the separated proteins. These three single polypeptides with molecular weights of 55 Kd–65 Kd and 110 Kd and Isoelectric point 5.1–5.8 demonstrated inhibition of binding of Celiac Disease patient serum IgA/IgG on the monkey esophagus and rat kidney/liver. Seven other monopolypeptides with molecular weight of less than 50 Kd inhibit binding to Gliadin.

In a preferred embodiment, the novel antigen of this invention is isolated by the following method:
   a) cleaning and washing a human placenta tissue with HEPES buffer;
   b) digesting the said placenta tissue with collagenase buffer to obtain a placenta cell population in suspension, said placenta cell population containing cytotrophoblast cells;
   c) enriching the cytotrophoblast cell population in said suspension via a 0–30% discontinuous Percoll gradient;
   d) extracting protein from said enriched cytotrophoblast cells with lysing buffer, extraction buffer and via ultracentrifugation to obtain a protein portion;
   e) isolating embryonic celiac antigen (ECA) from said exacted protein by applying said protein portion to an ion exchange DEAE Sephadex column followed by size exclusion gel chromatography; and
   f) identifying by SDS-PAGE and western blotting embryonic celiac antigens comprising protein molecules with an isoelectric range (pI) of from 5.1–5.8 and an apparent molecular weight selected from the group consisting of 55 Kd, 65 Kd, and 110 Kd and mixtures thereof.

While this is one proposed method for isolation of the novel antigen of this invention other suitable methods may be used.

Once the antigen of this invention (ECA) is prepared, sera of suspected celiac patients is added to well plates on which ECA has been immobilized. After incubation, excess antibody will be washed away and a horseradish peroxidase labeled secondary antibody directed at human IgA/IgG will be applied to the wells. The color changes will be read by the ELISA spectrophotometer reader. The antigen ECA will bind to the IgA contained in the sera of patients with Celiac Disease and this binding confirmed by the ELISA technique or procedures well known and described in Hekkens W T, Van Twist M: "Physiological role of antigliadin antibodies and their appearance in Celiac Disease" and "Serologic Diagnosis of Celiac Disease", Cleveland Press, 1990: 2A 21–58.

As above noted, in our search for a Celiac Disease antigen, we found that placenta tissue sections expressed an antigen which binds to the IgA contained in the sera of patients with Celiac Disease. We then identified, isolated and purified this antigen and designated this protein molecule as an Embroyonic Celiac Antigen (ECA).

Utilization of the newly discovered antigen: Develop a serologic diagnostic test for Celiac Disease which can be easily performed and objectively interpreted as a routine laboratory test. The isolated ECA protein will be immobilized as an antigen on a 96 well plate. Sera from patients suspected for Celiac Disease will be applied to the wells and assayed for the presence of reacting antibodies by Enzyme Linked Immunoassay (ELISA). The ELISA technique will be developed as the methodology for utilizing the ECA antigen as a screening test for Celiac Disease.

We recently identified that an IgA protein in the sera of patients with Celiac Disease binds to an antigen expressed on placental tissue sections. In those cases of IgA deficient celiacs on IgG antibody was found to bind to the placenta sections. Microscopic evaluation of placental tissue sections indicate that the antigen was expressed on chorionic villi, specifically on their surface and within the cytoplasm of these cells. We then established a primary culture of placental cell line grown first in 24 well plates and subsequently expanded to a 102 cm tissue culture flask. The cells in culture were found to express the ECA. An inhibition binding assay, however, demonstrated that the antigen was not secreted into the culture media by the placental trophoblast cultured cell line. The antigen appears to be located in the cytoplasm and on the cell surface.

Collected placenta culture cells were lysed using lysis buffer. Proteins were extracted from the culture lystate using ammonium sulfate precipitation. After dialyzed with PBS, the precipitated proteins were identified by the SDS-PAGE gel electrophoresis. Proteins extracted from the placental cell culture lysate were applied to SDS-Page Gel electrophoresis with a reducing and non-reducing condition reagent. Subsequently, proteins were transferred to nitrocellulose membrane and finalized with Western Blotting procedures described in Laemmli, U.K.: Cleavage of structural proteins during the assembly of the head of bacteriophage T4. Nature (London) 227:680, 1970.

Ten protein molecules were identified by the IgA contained in the sera of celiac patients. The molecular weights ranged from 17 Kd–110 Kd. In further experiments, using an inhibition assay, we proved that the isolated low molecular weight proteins (ranging 17 Kd–45 Kd) are gliadin-like polypeptides. These antigens were found to inhibit the binding of the IgA/IgG in the sera of celiac patients to gliadin antigens. During further identification of the rest of the antigens, we found two interesting proteins isolated from the placental cell line lysate. One exhibited a molecular weight of 110 Kd, and the other 65 Kd. These two proteins completely inhibited binding of IgA of Celiac Disease patients to rat kidney (Reticulin-like) and monkey esophagus (Endomysium-like). These two polypeptides were identified to have isoelectricpoints of 5.1 and 5.8. Using high pressure liquid chromatography (HPLC) we were able to purify these two putative Embryonic Celiac Antigens. An inhibition assay indicated that the 110 Kd protein inhibits at low concentrations binding of celiac patients' IgA to rat kidney. The 65 Kd protein, on the other hand, inhibited completely the binding of IgA to the monkey esophagus.

Both protein molecules had 60–70% of cross inhibition activity to either the rate liver or monkey esophagus. The 110 Kd protein is the heat labile protein and tens to break down to a 55 Kd molecule without losing the antigen binding activity.

We subsequently isolated the protein by the following two step isolation method. We first apply the crude extract protein isolated from the cultured placental cell lystate to a DEAE sephadex column and Gel Chromatography Sephacryl S-200 Hr Column (2.6×60 cm) and equilibrate it with phosphate buffered saline pH 7.3. We purified the 110 Kd protein in fraction collection number 40–45 and 65 Kd protein was purified in fraction collection number 55–60. The fraction samples were collected and purity was proofed by SDS-PAGE gel electrophoresis. Protein samples collected were concentrated and frozen for further usage.

The primary placenta culture cell line was established in our laboratory and was maintained at −70° C. until further usage. Using the fresh placental lysate additional 110 Kd was isolated. The frozen material, on the other hand, yielded more of the 55 Kd molecule which also is identified by the sera of celiac patients. The 110/55 Kd protein complex has the capacity to inhibit 100% binding of the celiac sera of rat kidney. We therefore hypothesize that this is a reticulin-like antigen. This molecule complex also inhibits 60% of the binding activity of celiac sera to the monkey esophagus. In distinction, the 65 Kd molecule inhibits 100% binding of celiac sera to the monkey esophagus. However, this molecule inhibits only 60% binding activity of celiac sera to the rat kidney. We therefore concluded that this is an endoymsial-like antigen and designate it as the ECA.

The above putative Embryonic Celiac Antigens isolated from a cultured human placental cell line does not bind to the IgA or IgG contained in the sera of normal patients, those with inflammatory bowel disease or other immunologic conditions.

1. Sample Preparation—starting with Human Placenta
   a. Wash the cells twice with PBS.
   b. Extract the washed cells with extraction buffer.
      Extraction buffer: 10 mM Tris-HCl, PH7.2
      0.15M NaCl, 0.02% $NaNO_3$ 5 mM Iodoacetamide
      2% NP 40, ImM PMSF 5 mM $MgCl_2$
   c. Centrifuge at 27000 g for 30 min, collect supernatant and store the extracts in liquid nitrogen.
2. SDS-Page
   a. Add sodium dodecyl sulfate (SDS) sample buffer, with or without DTT, to the sample solution and boil the final sample solution in water bath for 5 min.
   b. Perform SDS-PAGE (polyacylamide gel electrophoresis) in a Laemmli system with slab gel containing 10% or 12% acrylamide. (Ref. Laemmli, Nature 227, 680–685, 1970)
   c. Do silver staining with the gel. (Ref. Heukshoven, J. and Dermick. R, Electrophoresis, 6.103, 1985)
3. Western Immunoblot Analysis
   a. Transfer the proteins to nitrocellulose membrane in Bio-Rad Trans-Blot cell.
   b. Stain the gel with Coomassie brilliant blue after the transfer to confirm the uniformity of the transfer.
   c. Block the membrane with the TBST buffer (containing 0.1% Tween 20 in PBS) for 1 hr. at room temperature.
   d. Incubate the membrane with 1:500 dilution of CD patient serum (EMA titer 1:6000) in TBST buffer for 2 hrs. at room temperature.
   e. Wash the membrane three times with TBST.
   f. Incubate the membrane with a 1:2000 dilution of the goat antihuman IgA conjugated to horseradish peroxidase (Sigma, A0295) in TBST for 2 hrs. at room temperature.
   g. Wash the membrane three times with TBST.
   h. Incubate the membrane with ECL detection reagent for 1 min. and expose to XAR5 X-ray film (Eastman Kodak, Rochester, N.Y.)
   Ref:
      (1) Towbin, H., T. Staehelin and J. Gordin, Proc. Natl. Acad. Sci., USA 764350 (1979)
      (2) Bryon Batteiger, et al J. of Immunol. Methods. 55, 297–307 (1982)
      (3) Amersham Corporation ECL Western Blotting protocol booklet.

EXAMPLES

Example 1

Placenta Cell Line Preparation

Placentas were discarded tissue obtained from the Pathology department. The placenta were perfused with collagenase buffer containing 0.05% trypsin after flushing with Hepes buffer. Single cell suspensions were collected and different cell types were isolated and condensed from the mixture into various subpopulations based in their density characteristics using differential Percoll gradients. Cells from each isolation zone were cultured in RPMI 1640 medium conditioned with 20% fetal bovine serum (FBS). Non-adherent cells were removed 12–24 hours later.

Example 2

After rinsing with Hepes buffer, appropriate placental vasculature was catheterized using a 16 gauge angiocath, perfused with Hepes buffer for ½ hour, followed by a collaganase buffer digestion solution containing 0.05% trypsin for one hour. The placental tissue rich in chorionic villi was minced with scissors. The tissue mixture was allowed to digest while being constantly stirred and incubated at the 37° C. for a minimum of one hour. The singles cells were obtained by teasing apart the perfused placenta with forceps. The cells were pelleted by centrifugation (400×g) and washed twice with Fischer's medium.

Placental cells were obtained using density centrifugation with Ficoll-Hypoque and discontinuous Percoll gradient. A discontinuous Percoll gradient was made by carefully layering 70%, 50%, 30% Percoll (vol/vol) with 1× Dulbecco's (Gibco) PBS in centrifuge tubes. Pelleted cells were resuspended in a 10 mL Fischer's medium layered over the Percoll gradients and centrifigured at 800×g for 30 minutes at room temperature.

Several zones appeared in the Percoll gradient: 0–30% trophoblast cells, Stroma cells, small vessels and villous fragments, connective tissue elements, 30–50% Polymorphonuclear leukocytes, 50–70% Red blood cells, and mononuclear cells: Pellet: Red Blood cells. The 0–30% interface was separated and washed twice with Fischer's medium. Cells were plated into 25 $cm^2$ flasks with RPMI culture media containing 20% fetal bovine serum (FBS) and incubated at 37° C./5% $Co_2$/humidity-90% for 12–24 hours. The nonadherent cells were removed from the culture. The adherent placental cell line was propagated and expanded on 90 cm2 tissue culture flasks for further experiments.

Example 3

The collected placental culture cells were lysed using lysis buffer which contained 10 mM tris base, 5 mM Mg $Cl_2$;

0.15M NaCl; 2% NP-40; 5 mM iodoacetamide, 0.02% NaNo$_3$, 1 mM PMSF (phenylmethylsulfonyl fluoride) and adjusted the Ph to 7.0.

To identified protein contained in the placental culture cell line, the protein fraction was extracted from the placental cell culture lystate and applied to SDS-Page gel electrophoresis. The protein was applied to SDS-PAGE gel electrophoresis with a reducing and non-reducing condition reagent. Subsequently protein was transferred to Nitrocellulose membrane and finalized with Western Blotting. Ten protein molecule antigens were identified by the IgA in the sera of patients with Celiac Disease; at molecular weights ranging from of 17 Kd–110 Kd. In further experiments using an inhibition assay we proved that the isolated low molecular weight proteins (ranging 17 Kd–45 Kd) are gliadin-like polypeptides. These antigens were subsequently found to inhibit binding of the celiac patient sera (IgA-IgG) to gliadin antigens. During further identification of the rest of the antigens, we found 2 other proteins isolated from the placental stromal cell line lystate. One exhibited a molecular weight of 110 Kd, and the other 65 Kd. These proteins completely inhibited binding of IgA of Celiac Disease patients to the rat kidney (Reticulin like) and monkey esophagus (Endomysium like). These two polypeptides were identified to have isoelectricpoints of 5.1 and 5.8. Using high pressure liquid chromatography we were able to separate these two putative Embryonic Celiac Antigens. An inhibition assay indicated that the 110 Kd protein inhibits completely at low concentrations binding of celiac patients IgA to rat kidney/liver. The 65 Kd protein, on the other hand, inhibited completely the binding of IgA to the monkey esophagus. Both protein molecules had 60–70% of cross inhibition activity to the other substrate, i.e., rat liver or monkey esophagus. The 110 Kd protein is the heat labile protein and tends to break down to a 55 Kd molecule without losing the antigen binding activity.

Example 4

We subsequently isolated the protein by the following method from above mentioned placental culture lystate. Briefly, the method of isolation involves a two step isolation in which we use the crude extract protein isolated from the cultured placental lystate. The protein contained in the placenta lystate extract were first applied to a DEAE sephadex column (1.0×10 cm) previously equilibrated with 0.05M tris/HCL, pH 7.4. The absorbed components were subsequently eluted with 0.05, 0.1, 0.2, 0.3, 0.4, 0.5 M NaCl in 0.05M tris/HCL, pH7.4. The fractions were collected (2.0 mL each) and concentrated using ultrafiltration (Amicon Centricon-3). The concentrated DEAE samples were applied to the SDS-PAGE gel electrophoresis for protein identification. 0.2 M in 0.05M tris/HDL, pH7.0 eluted a 110 Kd proteins, 0.5M NaCl in 0.05M tris/HCL, pH7.0 eluted a 65 Kd major protein. Concentrated Chromatography protein fraction were applied and identified by the SDS-PAGE gell electrophoresis. DEAE chromatography collected samples were applied to the Gel Chromatography using Sephacryl S-200 HR Column (2.6×70 cm) and equilibrated with phosphate buffered saline pH 7.3. Samples were collected with 0.33 mL/min flow rate and 1 mL per tube. We purified the 110 Kd protein in fraction collection number 40–45 and 65 Kd protein were purified in fraction collection number 55–60. The fraction samples were collected and the purity were proven by SDS-PAGE gel electrophoresis. Purified and collected protein samples were concentrated and frozen for further usage.

The new antigen was isolated in our laboratory from a cell line established from placenta tissue. Two examples of its efficacy are: (1) indirect immunofluorescence staining indicates that this cell line expresses the antigen which binds to antibodies found in the sera of celiac patients, (2) the protein isolated from the crude extract of the primary placenta cell line binds as demonstrated by electrophoresis and Western Blotting to the IgA antibodies in the sera of celiac patients. 0.25 mg of the isolated ECA having a molecular weight of 65 Kd will inhibit binding of celiac patients serum to monkey esophagus or liver. On the other hand, 0.25 mg of isolated ECA having a molecular weight of 110/55 Kd will inhibit binding of celiac patients sera to rat kidney or liver but will not inhibit binding to monkey esophagus.

The screening process: Since the clinical presentation of Celiac Disease is quite variable, patients with symptoms such as chronic diarrhea, bloating, abdominal distention, short stature, growth disturbances and diabetes may require screening. Early diagnosis is important since treatment with a special gluten-free diet seems to reduce the risk of subsequent gastrointestinal malignancy. The diagnosis of Celiac Disease has required intestinal biopsy. A reliable noninvasive test for the disease has long been sought. The isolated ECA which binds the sera of Celiac Disease patients is a promising screening test. The ECA will be immobilized on 96 well plates. The sera of suspected celiac patients with the above symptoms will be added. After incubation, excess antibody will be washed away and a horseradish peroxidase labeled secondary antibody directed at human IgA/IgG will be applied to the wells. The color changes will be read by the spectrophotometer.

Below is a general outline of the procedure for producing the novel antigen of this invention:

1. Primary Placenta Cell Culture:
   Wash, perfuse and digest placenta tissue with hepes buffer and collagenase buffer—single cell suspension preparation.
2. Enrichment and concentration of the adherent cells from the cell suspension using discontinuous percoll gradient.
3. Protein extraction from the primary placental cell line using an extraction buffer and ultra-centrifugation.
4. Embryonic Celiac Antigen (ECA) Identification: Placental cell extracts were applied to SDS-PAGE gel electrophoresis to separate the proteins. Separated proteins were transferred to the nitrocellulose membrane (Western Blotting) incubated with the serum of patients with Celiac Disease. Horseradish-peroxidase conjugated rabbit anti-human IgA is applied to identify the binding of celiac patients IgA to the antigen. Ten monocomponent polypeptides were detected with Celiac Disease sera on nitrocellulose membrane. Three single polypeptides with molecular weight higher than 55 Kd (55 Kd–65 Kd and 110 Kd) and Isoelectric points 5.1–5.8 demonstrated inhibition of binding of celiac sera on the monkey esophagus and rat kidney/liver. Seven other monopolypeptides with molecular weights of less than 55 Kd did not inhibit binding.
5. Embryonic Celiac Antigen (ECA) Isolation: Initial separation of placental primary culture cell extract were done by injecting to the gell filtration (size exclusion) of HPLC Column from Bekman (Ultra Sphero Gell" (SEC 3000) size 5 micron. The column size is 7.5 mM×300 mM. Competition binding assay was used to identify the proteins. Separated proteins were also applied to the SDS-PAGE and Western Blotting to identify the purity and molecular weight of the proteins.
6. Embryonic Celiac Antigen (ECA) Isolation (Large volume separation using the gel chromatography):

Separation is performed using DEAE ion exchange chromatography and Sephacryl S-200 HR Column (2.6×) cm and equilibrate with phosphate buffered saline pH7.3.

Enzyme Link Immuno Assay (ELISA) Test Kit Development

ECA, the protein molecules reacting with Celiac Disease IgA and IgG were separated and purified from the primary culture of placental stromal cells. These proteins were coated to the 96 well plate. Serum from test patients will be applied to the plate and a secondary Horseradish-Peroxidase anti-human IgA antibody will be applied. Plates will be read using ELISA spectrophotometry reader.

A step-by-step procedure for the antigen ECA preparation is as follows:

(1) Primary Placenta Cell Culture:

Wash, perfuse, and digest placenta tissue with hepes buffer and collagenase buffer—Single cell suspension preparation.

(2) Enrichment and Concentration of the adherent cells from the cell suspension using discontinuous percoll gradient.

(3) Protein extraction from the primary placental cell line using an extraction buffer and ultra-centrifugation.

(4) Placental cell extracts were applied to the SDS-PAGE Gel Electrophoresis to separate the proteins.

(5) Separated protein were transferred to the nitrocellulose membrane (Western Blotting) incubated with the serum of patients with Celiac Disease.

(6) Horseradish-peroxidase conjugated mouse anti human IgA is applied to identify the binding of celiac patients IgA to the antigen. (10 monocomponent polypeptides could be identified by the IgA of sera from Celiac Disease patients on nitrocellulose membrane.)

(7) Separation of primary culture cells extract was done by injecting protein extract to the Gel filtration (size exclusion) of HPLC Column from Bekman "Ultra Sphero Gell" (SEC 3000) size 5 micron. The column size is 7.5 mM×300 mM.

(8) Competition biding assay was used to identify the separated proteins (Three single polypeptides with molecular weight higher than 55 Kd (55 Kd–65 Kd and 110 Kd) and Isoelectric point 5.1–5.8 demonstrated inhibition of binding of Celiac Disease patient serum IgA/IgG on the monkey esophagus and rat kidney/liver. Seven other monopolypeptides with molecular weight of less than 55 Kd inhibit binding to Gliadin).

(9) Large volume separation Using the Gel Chromatography Separation is performed using DEAE sephadex column followed by the Sephacryl Gel Chromatography S-200 HR Column, bed size dimension are 2.6×32 Cm.

Enzyme Link Immuno Assay (ELISA) Test Kit Development ECA, the protein molecules reacting with Celiac Disease IgA and IgG were separated and purified from the primary culture of Placental stromal cells. ECA will be coated to the 96 well plate. Serum from test patients will be applied to the plate and a secondary Horseradish-Peroxidase anti-human IgA antibody will be applied. Plate will be read using ELISA spectrophotometry reader.

The preferred and optimumly preferred embodiments of the present invention have been described herein and shown in the accompanying specification to illustrate the underlying principles of the invention, but it is to be understood that numerous modifications and ramifications may be made without departing from the spirit and scope of this invention.

What is claimed is:

1. An isolated antibody-antigen complex prepared by a process comprising contacting (1) an embryonic celiac antigen isolated by extraction from a cultured human placenta cell, said antigen comprising protein molecules with an isoelectric point (pI) range of from 5.1–5.8 and an apparent molecular weight selected from the group consisting of 55 Kd, 65 Kd, and 110 Kd, with (2) sera from a celiac disease patient.

2. The isolated antibody-antigen complex according to claim 1 wherein said antigen comprises protein molecules with an apparent molecular wight of 65 Kd.

* * * * *

UNITED STATES PATENT AND TRADEMARK OFFICE
CERTIFICATE OF CORRECTION

PATENT NO. : 6,653,085 B1
DATED : November 25, 2003
INVENTOR(S) : Amin Tjota

Page 1 of 1

It is certified that error appears in the above-identified patent and that said Letters Patent is hereby corrected as shown below:

<u>Title page,</u>
Item [73], delete "[73] Assignee: Xybernaut Corporation, Fairfax, VA (US)"

Signed and Sealed this

Sixteenth Day of March, 2004

JON W. DUDAS
*Acting Director of the United States Patent and Trademark Office*